(12) United States Patent
Neister

(10) Patent No.: US 8,481,985 B2
(45) Date of Patent: Jul. 9, 2013

(54) METHOD AND APPARATUS FOR PRODUCING A HIGH LEVEL OF DISINFECTION IN AIR AND SURFACES

(76) Inventor: S. Edward Neister, New Durham, NH (US)

(*) Notice: Subject to any disclaimer, the term of this patent is extended or adjusted under 35 U.S.C. 154(b) by 173 days.

(21) Appl. No.: 13/145,663

(22) PCT Filed: Jan. 29, 2009

(86) PCT No.: PCT/US2009/032392
§ 371 (c)(1),
(2), (4) Date: Jul. 21, 2011

(87) PCT Pub. No.: WO2010/087831
PCT Pub. Date: Aug. 5, 2010

(65) Prior Publication Data
US 2011/0272595 A1    Nov. 10, 2011

(51) Int. Cl.
*G01N 21/33* (2006.01)
*G21K 5/00* (2006.01)
*A61L 2/10* (2006.01)

(52) U.S. Cl.
USPC .... 250/504 R; 250/365; 250/372; 250/482.1; 422/24; 422/120; 422/121; 422/186.3; 210/748.1

(58) Field of Classification Search
USPC ............ 250/504 R, 365, 372, 492.1; 422/24, 422/120, 121, 186.3; 210/748.1
See application file for complete search history.

(56) References Cited

U.S. PATENT DOCUMENTS

| | | | |
|---|---|---|---|
| 4,317,041 A | 2/1982 | Schenck | |
| 5,843,374 A | 12/1998 | Sizer et al. | |
| 6,099,799 A | 8/2000 | Anderson | |
| 6,447,720 B1 * | 9/2002 | Horton, III et al. | 210/748.11 |
| 6,730,265 B2 * | 5/2004 | Horton, III | 422/24 |
| 7,326,387 B2 | 2/2008 | Arts et al. | |
| 7,808,170 B2 * | 10/2010 | Justel et al. | 313/486 |
| 2005/0186108 A1 | 8/2005 | Fields | |
| 2006/0188835 A1 | 8/2006 | Nagel et al. | |

FOREIGN PATENT DOCUMENTS

| WO | WO 2005/061396 A1 | 7/2005 |
|---|---|---|
| WO | WO 2007/084145 A2 | 7/2007 |

* cited by examiner

*Primary Examiner* — Nikita Wells
(74) *Attorney, Agent, or Firm* — Lambert & Associates; Gary E. Lambert; David J. Connaughton, Jr.

(57) ABSTRACT

This specification relates to an improved method, process and apparatus for disinfecting and sterilizing all types of surfaces and indoor air and room air contaminated with microorganisms. The improved apparatus consists of a multi-wavelength narrow spectral width UV source that is more effective than mercury based 254 nm germicidal lamps for destroying the DNA and outer shell or membrane of virus, bacteria, spores and cists.

14 Claims, 9 Drawing Sheets a. parallel irradiation b. perpendicular irradiation

Air Treatment in high volume ducts

Figure 1: Dimer Formation by UV Photon
(by permission of ERG @ UNH)

Figure 2: Bacillus atrophaeus after FUV photon impact

Figure 3: Serratia marcescens

Figure 4: Aspergillus Niger

Figure 5: Escherichia coli

Figure 6: Planktonic algae a. Side View - Dual Single Line Lamp b. End View with External Reflectors Figure 7. Dual - Single Line Lamp a. Hand held Surface Treatment b. Floor Treatment & Cleaner Figure 8: Surface Treatment a. Unprepared food b. Serving Counter Figure 9: Food Treatment a. parallel irradiation b. perpendicular irradiation Figure 10: Air Treatment in high volume ducts a. Top View b. Side View Figure 11: Caddie Disinfection Cart a. Top View b. Side View Figure 12: HVLS Room Disinfection

METHOD AND APPARATUS FOR PRODUCING A HIGH LEVEL OF DISINFECTION IN AIR AND SURFACES

BACKGROUND

1. Field of the Invention

This specification teaches an improved method and apparatus for disinfecting and sterilizing air, surfaces of all types and food from microorganisms. The method utilizes multi-wavelength UV photons that combine the effects of Far UV photons with UV-C photons to produce a higher level of disinfection than possible with either source separately. The apparatus consists of two separate chambers that produce the different wavelengths during the same excitation process.

2. Description of the Related Art

All prior art for sterilizing and disinfecting air has been based predominately on using commercially available germicidal ultra-violet (GUV) lamps. These lamps are either pulsed or continuously excited. Continuous lamps are mercury based and emit principally at 254 nm. A number of companies are presently producing GUV light based apparatus for the destruction of virus, bacteria, spores and pathogens that are in room air. This is an effective treatment because it continually exposes room air currents to the treatment light and over time has sufficient exposure time for treatment. The required exposure times range from 10's to 100's of seconds, depending on the light absorption capability of the different microorganisms at the 254 nm. While this is effective for treating the room air of individual rooms, it is not practical for treating large flowing volumes of air that pass quickly down large ducts. Its long treatment time requirement makes it impractical for treating most surfaces.

The broad ultraviolet spectrum has been divided into four regions depending on its different effects on biological systems. Reference to these regions are predominantly made in medical terminology with UV-A defined as a range or band between 320 nm and 400 nm, UV-B defined as a band between 280 nm and 320 nm, and UV-C defined as encompassing wavelengths shorter than 280 nm. Recently, the UV-C band has been further subdivided into two parts consisting of the Far UV (FUV) 185 to 250 nm and UV-C from 250 to 290 nm. Photochemists and Photobiologists do not generally use these terms because absorption spectra of chemical bonds are much narrower than these generally defined bands. Instead, they use the wavelength of the applied radiation to correlate to the observed effects.

Claims have been made that germicidal UV-C (GUV) radiation is used to deactivate DNA. This is because the mercury lamp emission at 254 nm is close to a good DNA absorption band. No claims are made that combine different wavelength UV photons to produce a higher level of deactivation of microorganisms. Furthermore, no claims are made that combine FUV photons with UV-C photons to produce a higher level of deactivation of microorganisms. A source of Far UV photons targets a nitrogenous base absorption band that has its peak absorption at 200 nm while a source of UV-C photons target other nitrogenous base absorption peaks (282 nm) as well as the amino acid absorption peak (254-265 nm). The application of multi-wavelength but narrow line UV photons produces an improvement in killing or deactivating pathogens compared to using either source of photons separately.

During the past few years, new UV emitting lamps based on the excitation of excimers are becoming commercially available. These emitters produce single line or narrow spectral emission at a wavelength determined by the gas composition of the lamp. If the treatment lamp's wavelength is chosen to match closely to the peak of absorption of the different component absorption bands of microorganisms, then a lethal dosage can be delivered to it in a shorter time. No patent has been found that teaches the use of FUV sources coupled with UV-C sources with supporting equipment that can effectively and efficiently disinfect and sterilize large volumes of air, large and small surfaces, and food stuffs in various stages of preparation.

In this specification, sterilization or sterilize refers to sterilization or high level disinfectant as defined by US FDA. Disinfectant or disinfection refers to all other levels of disinfection.

BACKGROUND

The genetic makeup of all living organisms is contained in their DNA molecule. Replication occurs by the splitting of the DNA molecule, which duplicates itself through a transformation of its structure. Parts of the DNA molecule have been given names such as pyrimidine bases, cytosine, thymine or uracil that form a group of biochemicals that sustain life. The long DNA molecule holds itself together by using simple bonds like those found in sugars.

Figure 1:
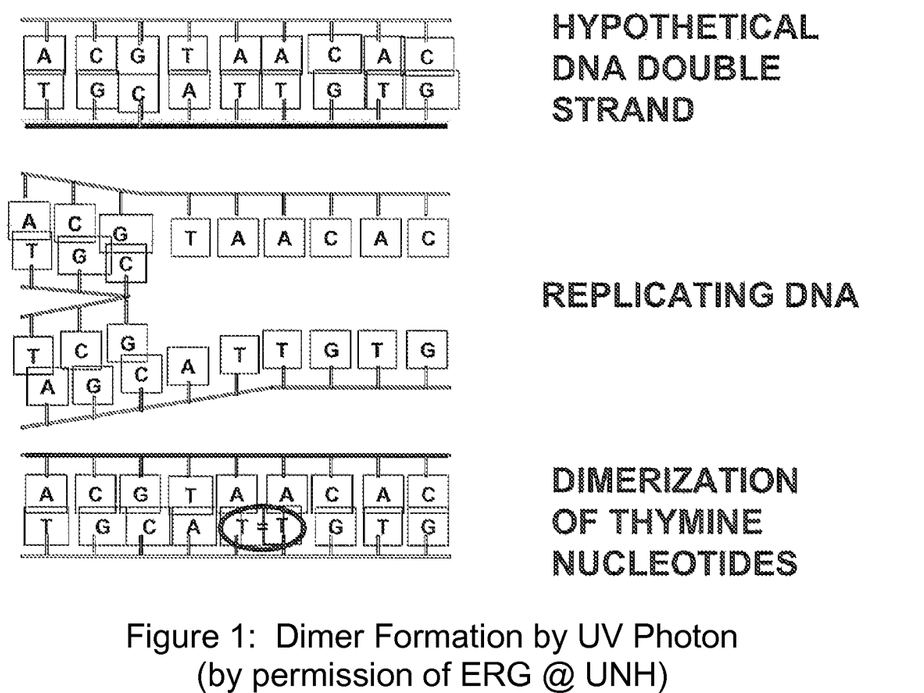
FIG. 1 is a graphic showing dimer formation in a DNA molecule.

Researchers believe that the energy of the GUV photon causes the formation of a strong (covalent) bond to develop between specific biochemicals. However, the bond strength of the covalent bond is very dependent on the relative position of the participating atoms. When the bond is symmetrical on both sides of a hydrogen atom in the bond, it is referred to as a dimer. A dimer is a very strong bond and is not generally broken during the vaporization of the liquid. GUV light is known to produce Thymine, cytosine-thymine, and cytosine dimers. After the formation of the dimer, further replication of the DNA stops. FIG. 1 shows the concept of the dimer formation in a DNA molecule. Reports found in literature have demonstrated that UV photons at other wavelengths or low wavelength blue light can promote repair of the injured bonds and permit the organism to start replicating again. This is commonly referred to as photo-reactivation.

The DNA molecule absorbs light from about 180 nm to about 400 nm. The commercial germicidal lamps based on mercury excitation are used because they emit photons that are near the 260 nm absorption peak of DNA amino acids. The mercury gas and its pressure in the lamp determine the wavelength of the emitting light. For low-pressure (LP) and low-pressure high output (LPHO) lamps, the emitting wavelength is 254 nm. For medium pressure lamps, the emission ranges from 200 nm to above 400 nm. However, the strength of the emitted light is not effective below 245 nm for the continuous emitting lamps and below 235 nm for medium pressure lamps. Xenon gas in pulsed lamps produces a similar multi-wavelength emission to the medium pressure mercury lamps. However, critical to this patent is that the multi-wavelength source produces two different narrow spectral width (commonly referred to as single line) emissions that correspond to at least two peak absorption chromophores of the microorganism's DNA. This source is now referred to in the rest of the patent as a dual-single line lamp.

DNA action spectra show multiple peaks that are dependent on the composition of the nitrogenous bases and amino acids that make up the organism. While FUV photons have shown to be effective in breaking bonds, it is possible that the correct dual wavelength combination of FUV and UV-C could be just as or more effective. (See U.S. Pat. Pub US 2010/0028201.)

A recent technical paper (Peak et al, UV action spectra for DNA dimmer induction . . . , Photochemistry and Photobiology, 40, 5 (613-620), 1984) suggests that dimmer formation is not the only requirement to inactivate DNA. Absorption of different wavelength photons by different molecular groups in the long DNA molecule will enhance the energy transfer from group to group. Damaging or destroying these bond groups may be more effective in deactivating the DNA than with photons in a single band that affect only a few groups. No one has done a detailed study of the effectiveness of inactivation for the different single line UV emitters working in combination.

There are many articles about multi-photon effects on materials that can create different processes because different photon energies will resonate or create different energy levels in the electrons or atoms of the molecule. The concept in this specification is to use multiple narrow line wavelengths emitted from the same lamp to create multiple absorption pathway effects on microorganisms. It is conceivable that greater damage and a larger reduction in survival can occur since the multi-photon interaction could have more pathways to create its destruction. These pathways can occur simply by resonant absorption that causes a physical breaking of bonds in the pathways. It could also cause significant cross linking of different amino acids, nitrogenous bases, nucleotides and other critical bonds that permit the organism to replicate. Cross linking these bonds could and should create conditions that the organism could not replicate further and would reduce the transmission of these infectious agents to people in the area.

The energy of the emitted photon is determined by its wavelength. Photon energy is about 5 ev at 250 nm, and increases for shorter wavelengths. Different bonds in the DNA will be affected with photons of different energy.

Figure 2:
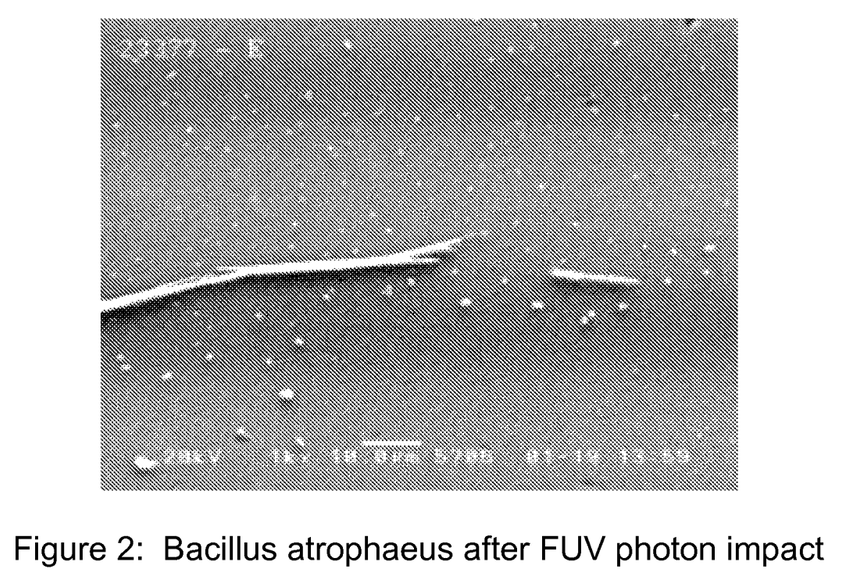
FIG. 2 is a micrograph of the *Bacillus atrophaeus* with magnification of 300× and 1000×.

The 540 kJ/mole photon energy from the FUV lamp exceeds the bond energies of many of the peptide bonds in proteins and those in nitrogenous bases of the DNA. The bacterial cell is surrounded by a lipid membrane or cellular wall that contains many protein molecules. The cell wall is essential to the survival of many bacteria. FUV light can damage the proteins in this structure whereas GUV can not. This should cause physical damage to the microorganism. FIG. 2 shows a micrograph of the *Bacillus* atrophaeus with magnification of 1000×. Photon impact resulted in ruptured sidewalls and organism segmentation that can be clearly seen in the 1000× frame. This is the first photographic evidence known that photons are actually causing damage and destruction to pathogens. A corresponding slide that received the same radiant exposure did not produce any replication indicating 100% kill of the organisms.

It has been fairly well established that the peptide bonds in all proteins are responsible for the peak absorption at two different wavelength regions; namely at 200 nm and at 280 nm. The peak absorption at either 200 nm and/or near 280 nm is also exhibited by all nitrogenous bases in the DNA as well as the proteins that form the outer cellular membrane of bacteria, spores and viruses. This occurs as well for nucleoproteins, diglycine, triglycine, and bovine albumin (McLaren, et al, Photochemistry of Proteins and Nucleic Acids, Pergamon Press, Macmillan Company, 1964). Amino acids have a peak absorption band near 260 nm. A UV lamp emitting at 222 nm and/or 282 nm will produce the greatest photon absorption by the nitrogenous bases and proteins. A UV-C lamp emitting at 260 nm will produce the greatest photon absorption by the amino acids in the DNA. Consequently these three wavelengths are primary absorption bands that permit destruction of microorganisms.

Tests:

A number of comparative tests were done using three different microorganisms to test the concept. Petrie dishes were inoculated with each organism and exposed to different combinations of UV photons. The included figures show the same dish with light and dark background in order to get good contrast of the results.

Figure 3:
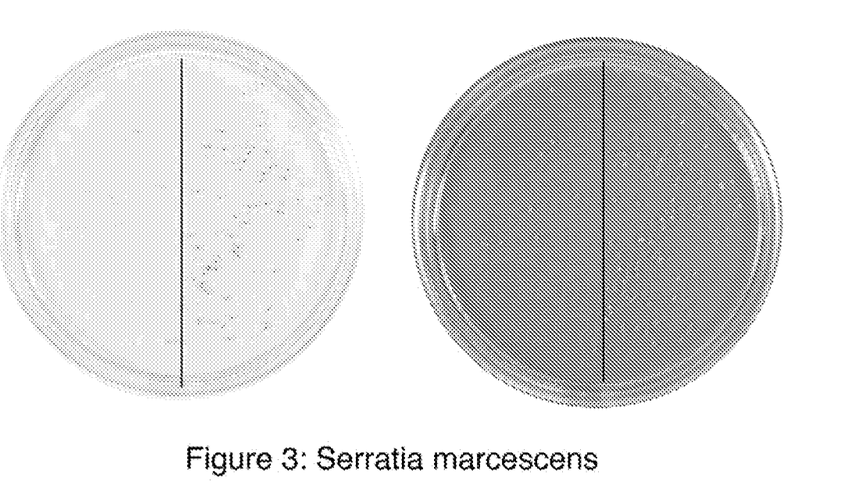
FIG. 3 is *Serratia marcescens* as the test organism.

FIG. 3 had *Serratia marcescens* as the test organism. The left side of the dish was exposed with a combination of 222 nm plus 254 nm photons. The right side of the dish was exposed with only 282 nm photons. The multi-wavelength side produced a significant improvement.

Figure 4:
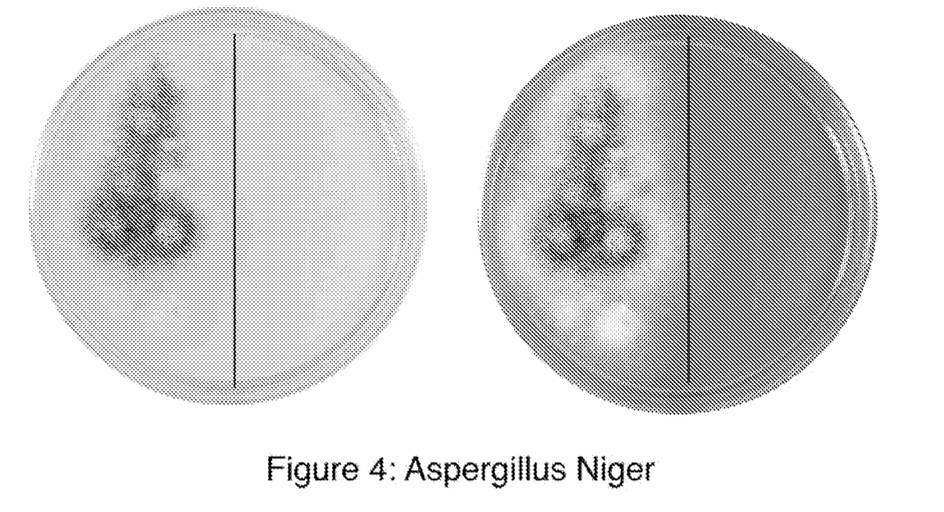
FIG. 4 is *Aspergillus Niger* as the test organism.

FIG. 4 had *Aspergillus Niger* as the test organism. The left side of the dish was exposed with only 282 nm photons. The right side of the dish was exposed with a combination of 282 nm plus 254 nm photons. The multi-wavelength side produced a significant improvement.

Figure 5:
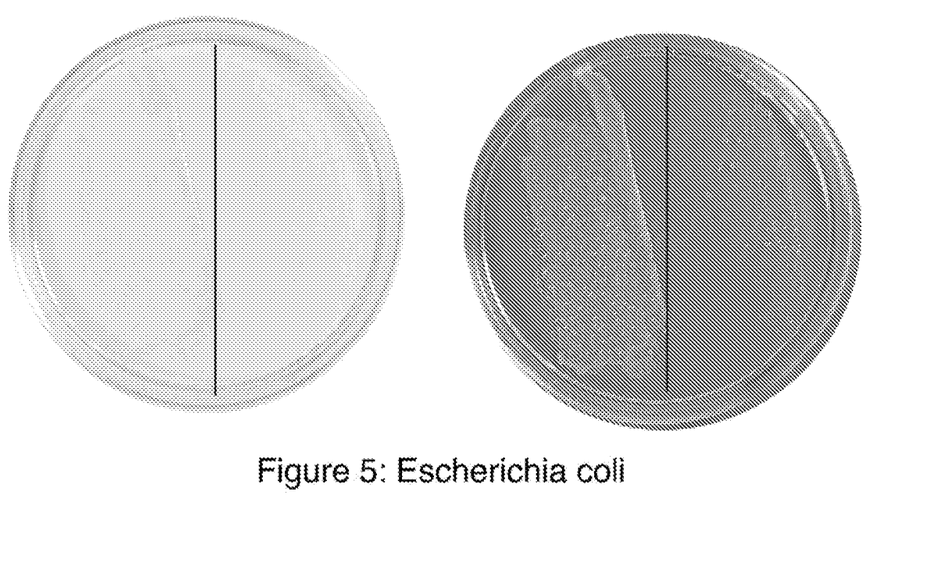
FIG. 5 is *Escherichia coli* as the test organism.

FIG. 5 had *Escherichia coli* as the test organism. The left side of the dish was exposed with a combination of 222 nm plus 254 nm photons. The right side of the dish was exposed with a combination of 282 nm plus 254 nm photons. The right side using the correct multi-wavelength combination of photons produced a significant improvement.

Figure 6:
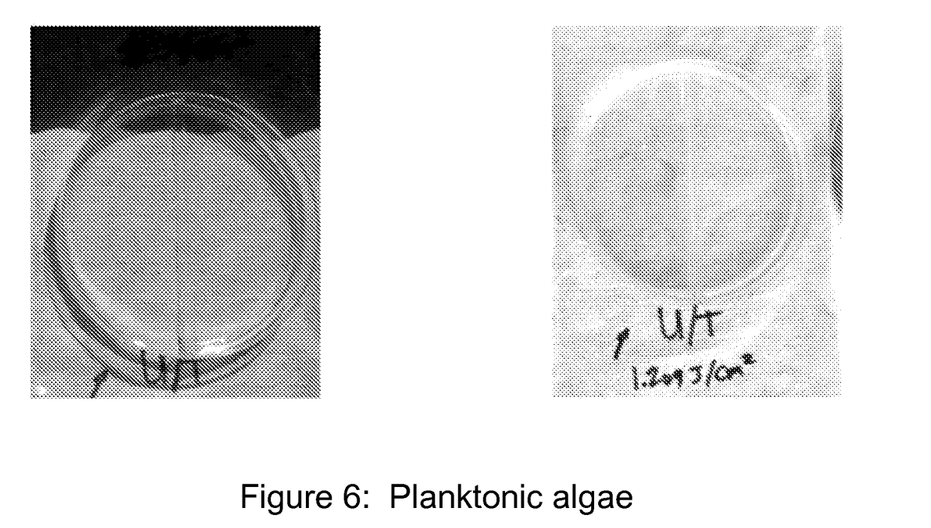
FIG. 6 is Planktonic Algae as the test specimen.
Figure 7:
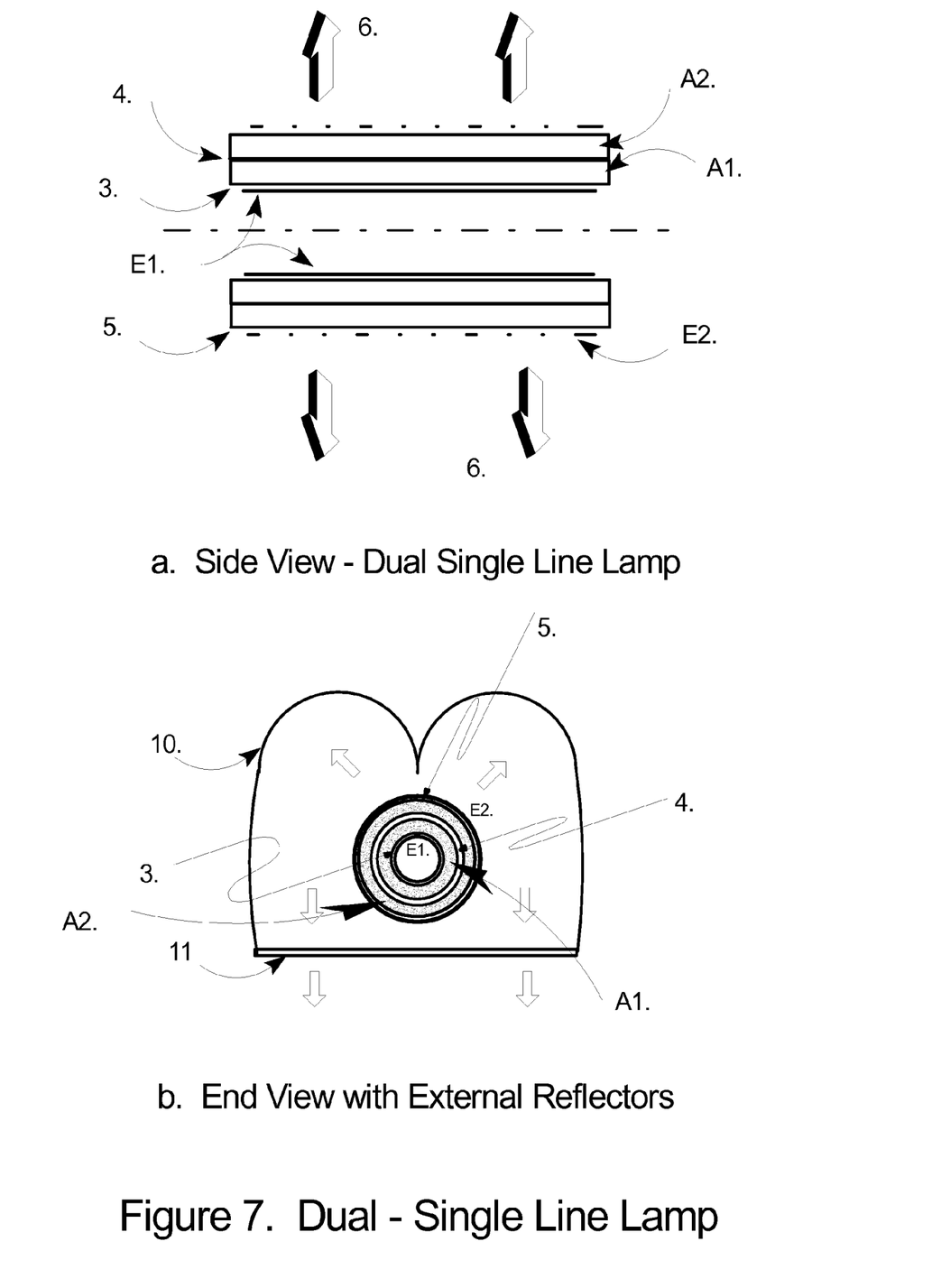
FIG. 7 is a perspective schematic view of a preferred embodiment of the present invention defining the location of important components of the dual-single line lamp therein.
Figure 8:
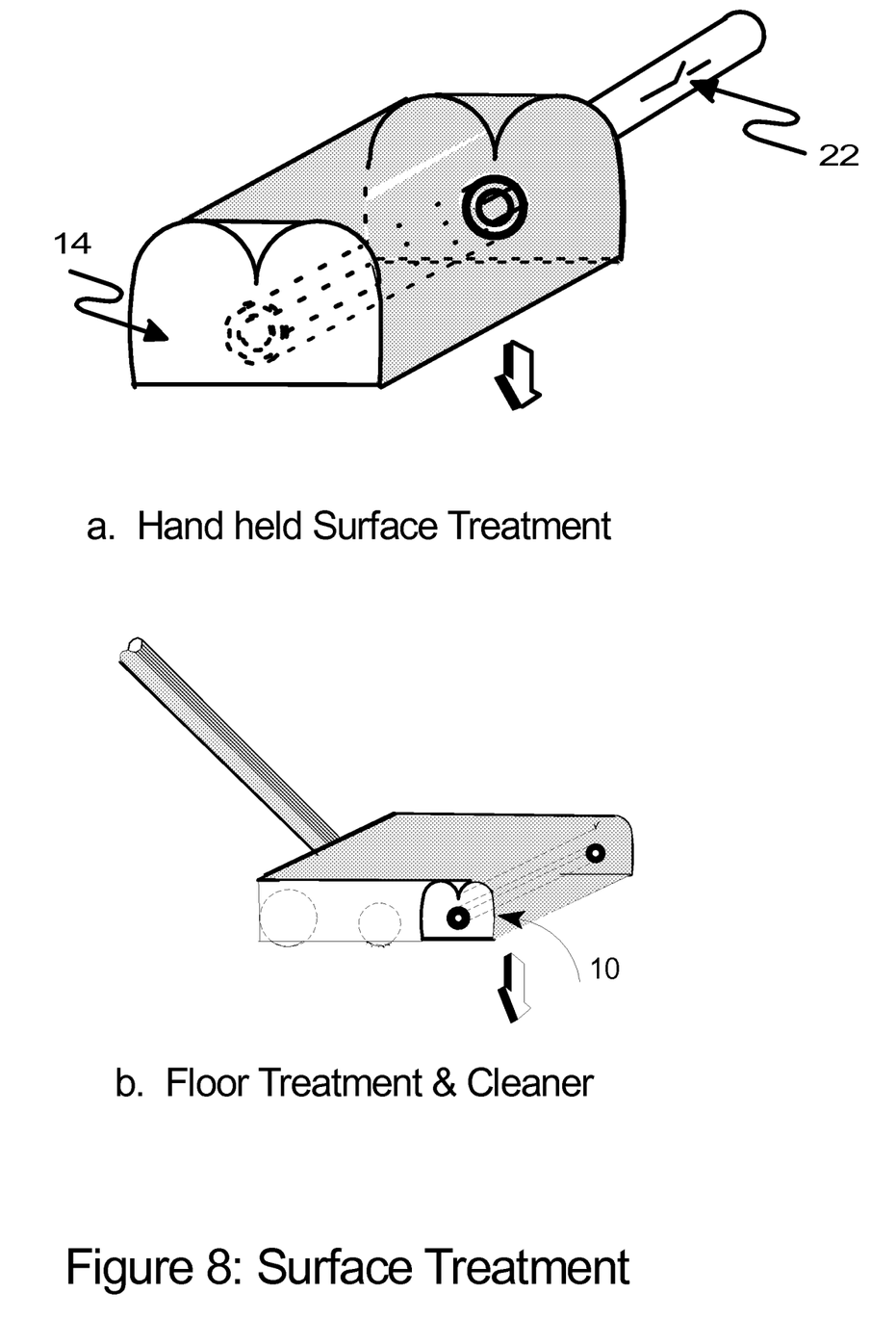
FIG. 8 is a perspective schematic view of a preferred embodiment of the present invention defining the location of important components for disinfecting or sterilizing surfaces such as chairs, hand rails, counter tops, trays, table tops and floor surfaces and the like therein.
Figure 9:
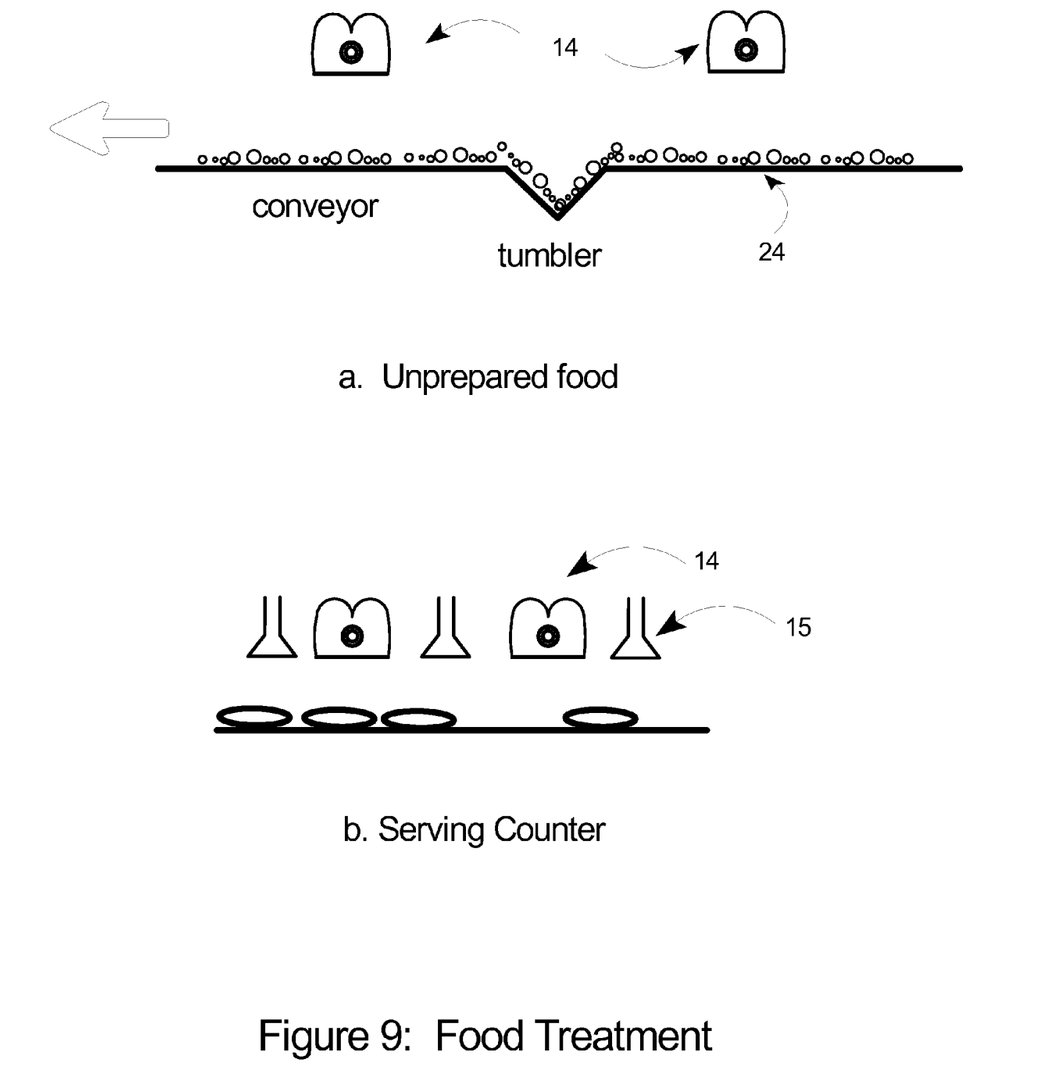
FIG. 9 is a perspective schematic view of a preferred embodiment of the present invention defining the location of important components for disinfecting food prior to handling by kitchen or cooks before serving therein.
Figure 10:
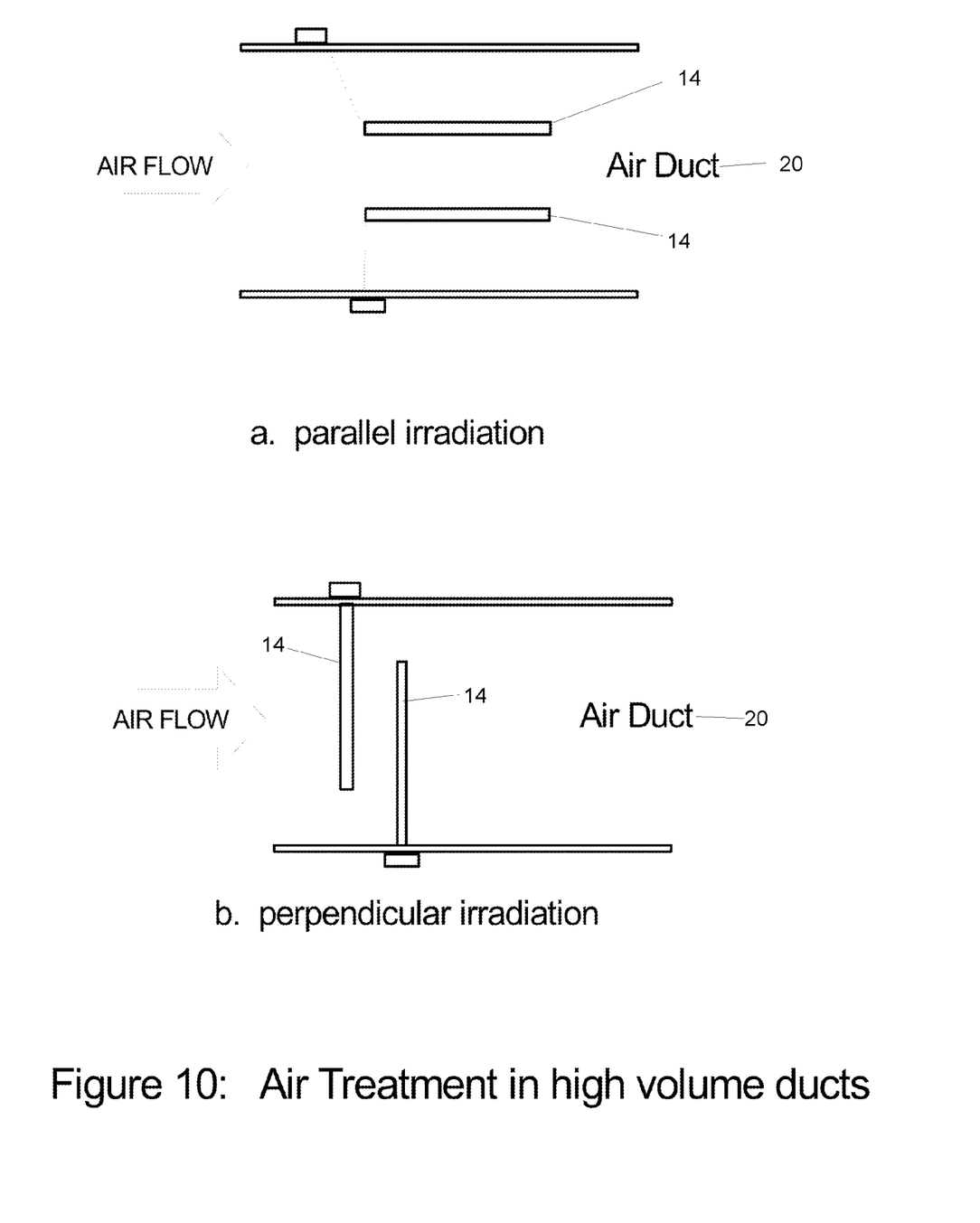
FIG. 10 is a perspective schematic view of a preferred embodiment of the present invention defining the location of important components for disinfecting or sterilizing air flowing inside air ducts therein.

FIG. 6 had Planktonic Algae as the test structure. The left side of the dish was not exposed but the right side was exposed to FUV photons. Significant cellular damage occurred.

Analysis:

All tests were done using single line photon sources that emitted near the peak absorption of the two absorption bands of the DNA nitrogenous bases and the single absorption band of the DNA amino acids. This provided a true measure of the photon interaction for each of the different chromophore molecular groups and the interaction with other chromophore groups in the DNA molecule.

The results of the first three tests showed significant reduction in living organisms when multi-wavelength narrow line photons were used compared to single wavelength photons. These tests also demonstrated that the correct combination of dual-single line photons were significant and dependant on each organism. FIG. 6 demonstrates that the choice of wavelength is important. FUV photons produce significant cellular damage where GUV photons have little effect.

Similar tests done on pathogens would produce a list of the most effective combination of photon wavelengths that are effective in killing or deactivating each pathogen.

SUMMARY OF THE SPECIFICATION

Critical to this method is the development of a dual-single lined lamp that emits at least two narrow wavelength bands of ultra-violet photons that match closely to the maximum absorption bands for DNA chromophores of nitrogenous bases, proteins, amino acids and other component bonds of microorganisms. The preferred embodiment is a multi-wavelength narrow line source emitting at least two different wavelengths. This spectral emission is significantly more effective than standard 254 nm photons for destroying DNA. Kill action times are reduced from 10's to 100's of seconds to times of 0.1 seconds. The dual-single lined lamp can kill pathogens in the air on the fly as they pass by. This dual-single lined lamp is also effective for the breakdown of biofilm and protein based allergens.

Photon energy of the dual-single line lamp where one line is in the FUV is sufficiently high to break carbon bonds of chemical toxic substances with similar action times. Unique to obtaining short action (kill) times is a determination of the specific wavelength required to destroy the targeted organism or chemical. The dual-single line source is chosen to supply at least two narrow emission bands of UV light that are close to the peak absorption of at least two principal absorbing chromophores of the targeted organism or chemical.

The relative intensity of one line compared to the other can also influence the kill or deactivation efficiency. If the annulus of each chamber in the triax tube is the same width, then the intensity of the light from the outer annulus will be greater than the light emitted from the inner chamber if the gas density is the same for both. Over six combinations of gas density and annulus location can be produced in a single triax lamp design. Adjustments in gas density and location provide for a photon emission combination that is most effective for all of the major pathogens that are desired to be killed or deactivated.

This apparatus makes for a cost effective improved method for sterilizing and disinfecting air, all types of surfaces, and food during normal daily activity. (See FIGS. 7-10.) Furthermore, the apparatus is capable of effectively and efficiently disinfecting floors, hand rails, and objects that are in constant contact with transient populations. Routine disinfection of these areas should significantly reduce the transmission of disease and toxic substances that can cause injury or illness to people and animals.

The dual-single line lamp radiation can be applied to any object or surface that needs to be disinfected and/or sterilized. An example would be the use of a caddie cart positioned outside a patient room. All instruments, papers and pens used in the room would be passed through the caddie cart and exposed to the dual-single line lamp radiation as they leave the room. (See FIG. 11.) This procedure would prevent the transmission of pathogens to the next patient. Testing will also determine the correct exposure limits and prevent any harmful effects that could occur when used to disinfect human skin and wound areas, hands, animal surfaces such as skin, fur, and hair, and critical plastics and materials used in medical devices, Because the dual-single line lamp source is a light source, it can be directed to expose different levels of thick and loose materials by using light conducting fibers to distribute the light intensity. An example would have the dual-single line lamp source disinfecting a floor by directing it at the floor while some of the light is directed to the bottom of a rug or floor scrubbing brush by light fibers imbedded in the brush. In a similar manner, products that have cavities or areas not exposed directly by the external source could be disinfected. An example of this would be a single fiber used to direct dual-single line lamp into a tooth cavity to disinfect the walls and tissue inside prior to adding the filling.

The dual-single line lamp source can be used to directly disinfect room surfaces, apparatus, fixtures and clothing and microbes in the room air by directly exposing all objects for the required exposure time. Several sources can be combined to assure exposure to all surfaces and to reduce total exposure time. It can provide effective treatment to isolation room air by preventing pathogens from remaining alive after exiting the room. Rooms contaminated by bioterrorist agents could be treated by using robots to move the dual-single line lamp source(s) in many directions and moving it (them) around the room during treatment.

A major source of infection and terrorist's activity is directed at food and material handling. Photon emitters have been used to effectively clean food stuffs and surfaces for many years. However, this invention uses the dual-single line lamp source that makes it cost effective in treating surfaces of food and materials since the action time is almost immediate.

The dual-single line lamp source is an improved method for producing a dry chemical free disinfection of food stuffs. It can be used to disinfect seeds and sprouts prior to planting, food raw stock preparation for transportation from the fields to processing centers, to warehousing and storage, to supermarket handling and kitchen preparation and delivery to the consumer. Furthermore, it can be used to disinfect cutting and working surfaces of meat and poultry packaging rooms and even the cutters and equipment used to transport and process meat, produce and other food products.

The apparatus of this invention is capable of irradiating food stuffs in conveyor assemblies, stationary carts and in handling routes during the movement from storage to food preparation processes. It can also be used to sterilize/disinfect medical or critical parts on an assembly line prior to packaging.

There is increasing evidence that room air disinfection could be important to reducing infections of microbes carried by small aerosols created by sick people when they cough or sneeze. Currently, room UV disinfection has been limited to using mercury based germicidal lamps placed on walls having shields to ensure that no people could be irradiated. These generally do not incorporate fans but rely on room air currents to cause the microbes to pass by the light. A second concept uses a box having one or more GUV mercury lamp in the out flow air stream of a fan or blower. This box is placed in appropriate positions of the room in hopes of capturing the microbes and causing them to pass over and by the lamps. In both cases, only 50% of all the microbes in the room are exposed as reported in literature.

The dual-single line lamp installed in a different type of apparatus will permit exposures up to 90% of all microbes for each pass. The new supporting apparatus is based on the fact that large volumes of air can be moved more effectively by creating conditions that take advantage of normal drafts and circulation room air currents caused by the difference in room air temperatures near the ceiling compared to the floor. This apparatus uses either 4 or 5 blade paddle fans operating at slow speeds or special fans developed for best efficiency to assist the rising of air, directing it into an upper room air zone that could be irradiated by either dual-single line or multiple single line lamps (See FIG. 12). The lamps would be positioned above the fan to irradiate the rising air column in all directions. Baffles would prevent light from penetrating into the occupation zone. During the relatively long resonance time of any microbes in the air zone, a large fraction would be killed or destroyed. Each pass could destroy over 90% of all the microbes in the zone. After three passes in an hour, 99.9% would be destroyed for an effective removal of 3 log reduction.

DESCRIPTION OF THE PREFERRED EMBODIMENTS

The drawings illustrate the invention in its different forms and the apparatus required to make a dual-single line lamp. The lamp consists of a triaxial tube that has two annuluses which contain the different gas mixtures to produce different wavelength photons when the lamp is electrically excited. The middle tube diameter is chosen to optimize the relative intensity emitted from both chambers. Excitation of both gases occurs when high voltage is applied between an electrode placed on the inside of the inner tube and an electrode placed on the outside of the outer tube. A screen is used as the outer electrode to permit light emission to pass outwardly from the lamp.

FIG. 7a illustrates a cross section of a dual-single line lamp that forms part of the disinfecting apparatus of the present invention. The high voltage electrode E1 is located inside the inner tube of the dual annular lamp. The ground electrode screen E2 is located on the outside of the dual annular lamp. One gas that produces the UV photons is located in the annular region A1 between the inner 3 and middle tube 4. A second gas that produces the UV photons is located in the annular region A2 between the middle tube 4 and the outer tube 5. The gas types are chosen so that the emitted UV photons are absorbed by the targeted microorganism or chemical. UV radiation is emitted radially outward 6. Changing the voltage or current between the two electrodes changes the amount of UV radiation that is produced. Changing the dimensions of each annulus or the gas density in each annulus changes the relative intensity of one chamber compared to the other. The preferred embodiment is to choose the gas composition in each chamber to produce a FUV wavelength at 222 nm and UV-C wavelengths at or near 254 nm and 282 nm. Three different dual-single line lamp combinations can be made from the combination of three different wavelengths.

FIG. 7b illustrates the dual-single line lamp used to direct the UV photons towards a specific location, direction, surface, material or substance. The dual-single line lamp is shown in the center of the drawing as an end view. The specialized reflector 10 end view incorporates a specialized 'gull wing' design so that >90% of the emitted light is directed to the planar surface below. The specialized reflector 10 also incorporates barium sulfate ($Ba_2SO_4$) as the reflective material in order to maximize the number of photons that are reflected onto the planar surface. In some cases, a cover 11 is necessary to protect the NUV source and reflector from dirt. This cover is transparent to the UV light. The specialized reflector can also have different shapes that change the directed radiation for different applications.

FIG. 8a illustrates a preferred embodiment with the dual-single line lamp contained in a hand held wand. The wand is used to disinfect commonly touched objects that act as fomites to transmit pathogens from one person to the next. Sensing switches can be included in this embodiment 22 that shut off the dual-single line lamp when the dual-single line lamp is not directed correctly to the desired treatment surface. The wand would provide a means for wound treatment prior and post surgery and for the treatment of chronic wounds. It is also provides a means to disinfect hospital and health care rooms, operating tables, hand rails and equipment surfaces that support patient care.

Furthermore, in cases of critical shortages of gloves, robes and masks, the dual-single line can be used in a similar manner to disinfect these items periodically when appropriate instead of retrieving new ones from supply.

FIG. 8b illustrates the dual-single line lamp located inside the forward compartment of a vacuum cleaner or floor cleaning machine. The vacuum cleaner can be either a standup floor model or a canister model. It could also be any device that would support and carry the dual-single line lamp close to the floor. The significant part is that the dual-single line lamp with reflector 10 consists of the components as described in FIGS. 7a and 7b. As shown, the components comprise a box, wheels, and a handle.

FIG. 9a illustrates the dual-single line lamp located above a conveyor that carries raw and unprepared food prior to kitchen preparation as well as industrial packaging assembly lines that carry products that require disinfection. The conveyor assembly 24 is designed to maximize the surface area exposed to the dual-single line lamp(s). In some cases, several lamps 14 are required because the exposed surface of the food or product can not be changed to expose the entire surface during the illumination time of one dual-single line lamp. Tumblers or vibrators are typically used to change the orientation of the foodstuffs and they move along the conveyor. FIG. 9b illustrates the dual-single line lamp 14 located beside heat lamps 15 or other heating surfaces used to keep the food hot on a serving counter prior to being delivered from the kitchen to the customer. In another embodiment, the dual-single line lamp is used to irradiate cool or cold foods, so heat lamps 15 are not used.

In use, the dual-single line lamp can be made to any size and length. In air ducts 20, the preferred embodiment FIG. 10a would have the dual-single line lamps 14 supported from the side, top or bottom of the duct 20 so that its axis is parallel to the airflow. For unique applications, a second embodiment FIG. 10b would have the dual-single line lamp sources 14 and cylinder reflector supported inside the duct 20 so that its axis is perpendicular to the air flow. An example of this embodiment would be a dual-single line lamp positioned in the center of a cylindrical tumbler. All objects would be irradiated during the tumbling process for a length of time that would guarantee disinfection.

Figure 11:
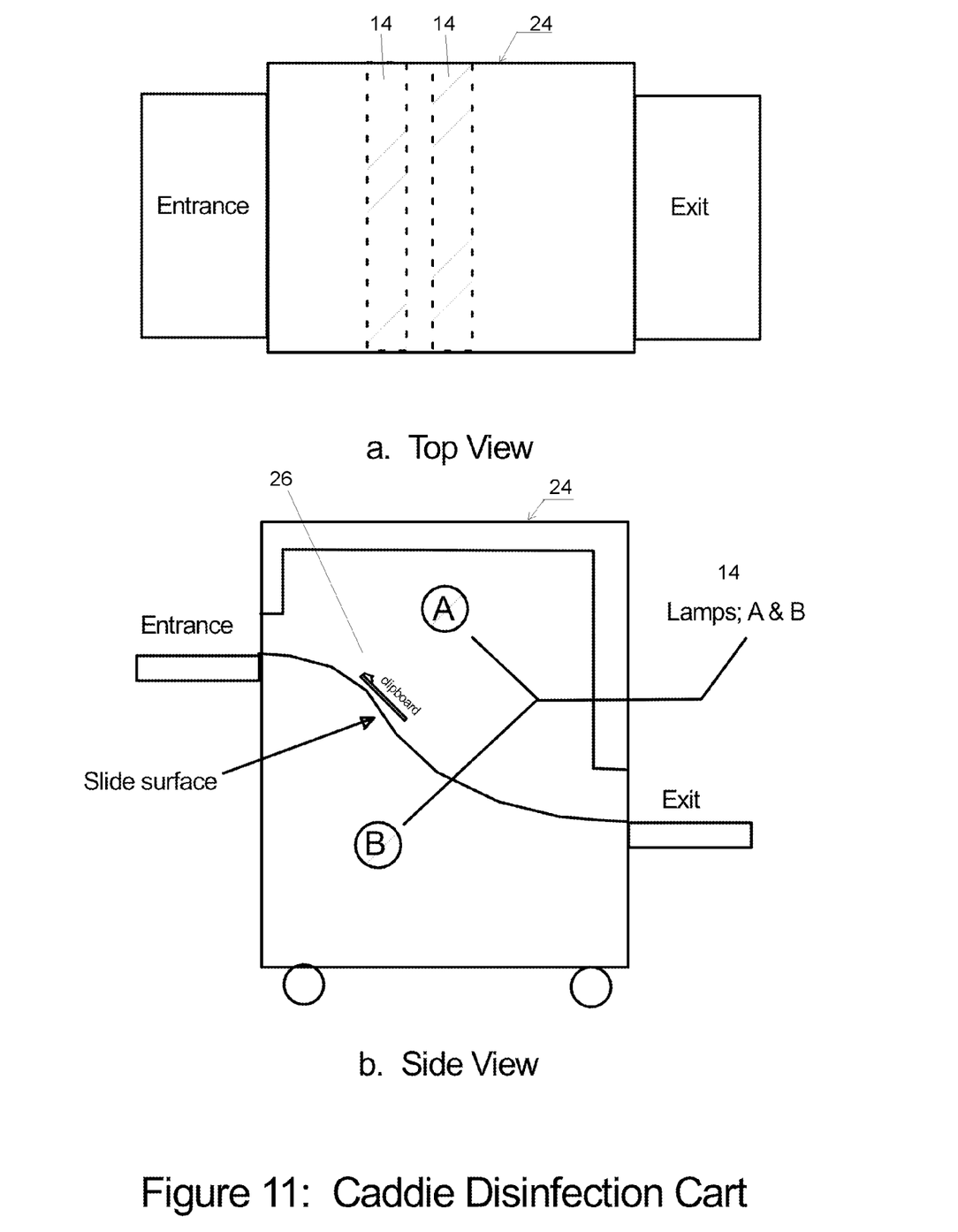
FIG. 11 is a perspective schematic view of a preferred embodiment of the present invention defining the location of important components for disinfecting or sterilizing surfaces of materials and objects that pass through a portable caddie therein.

FIG. 11 illustrates the dual-single line lamp(s) used to disinfect patient examining tools, records, pens and equipment 26 between patients. Everything that is brought into the room for examining the patient should be passed through the irradiation zone in the medical caddie 24 after exiting the room. It is retrieved only after the doctor or health care administrator changes to a new set of gloves and other pertinent garments.

Figure 12:
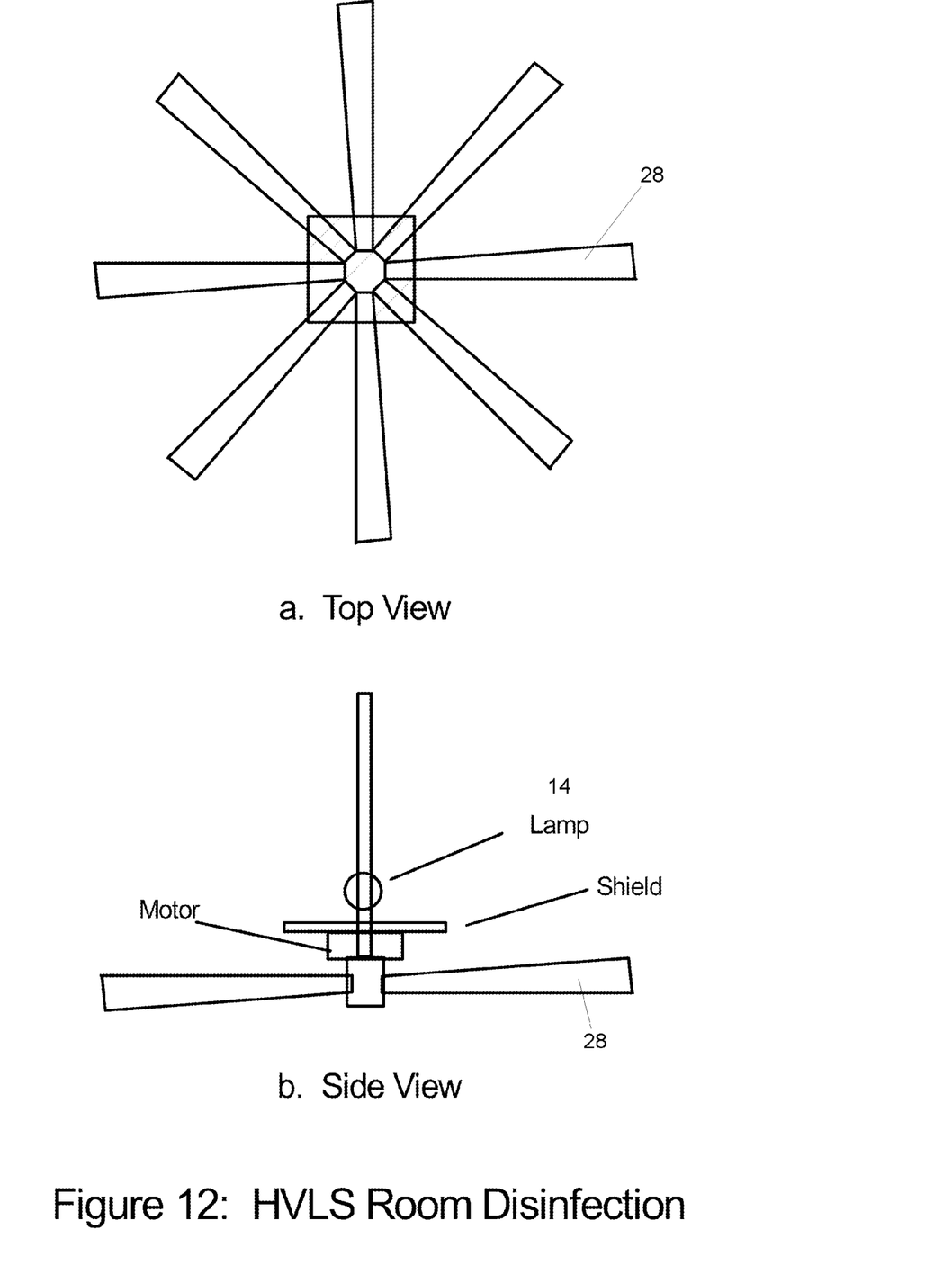
FIG. 12 is a perspective schematic view of a preferred embodiment of the present invention defining the location of important components for disinfecting or sterilizing room air as it is moved through the room using a high volume low speed (HVLS) ceiling fan therein.

FIG. 12 illustrates a preferred embodiment with the dual-single line lamp mounted above a high speed low velocity fan 28 to disinfect room air.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A disinfecting apparatus comprising:
    a dual-single line lamp comprising:
        three triaxial tubes defining two annuli there between;
        a first gas mixture selected to produce a first narrow wavelength photon emission; and
        a second gas mixture different from the first gas mixture selected to produce a second narrow wavelength photon emission that is different from the first narrow wavelength photon emission;
        a high voltage electrode located on a first tubular surface of one of the three triaxial tubes;
        a ground electrode located on a second tubular surface of one of the three triaxial tubes, the second tubular surface located opposite the two annuli from the first tubular surface; and
    a photon reflector secured in a spaced relationship to the dual-single line lamp positioned to direct photons to a zone or surface, whereby the disinfecting apparatus produces photons that are directed to a selected zone or surface and efficiently destroys or deactivates DNA organic bonds and proteins of microorganisms when the high voltage electrode is energized.

2. The disinfecting apparatus of claim 1, wherein the first and second narrow wavelength photon emissions are taken from the group consisting of 222 nm, 254 nm, and 282 nm.

3. The disinfecting apparatus of claim 1, wherein at least one lamp is an excimer lamp.

4. The disinfecting apparatus of claim 1, wherein the photon reflector is a gull wing-shaped director selected to direct at least 90% of emitted light to a planar surface.

5. The disinfecting apparatus of claim 1, the photon reflector comprising a barium sulfate composition for enhancing its reflective properties.

6. The disinfecting apparatus of claim 1 further comprising a box, wheels, and a handle suitable for use as a floor cleaning apparatus.

7. The disinfecting apparatus of claim 1 further comprising:
    a handle attached to the dual-single line lamp; and
    a surface detection mechanism adapted to shut off the dual-single line lamp when it is not near a surface to be disinfected.

8. The disinfecting apparatus of claim 1 further comprising:
    an air duct surrounding the lamp mounted in a spaced relationship to the lamp to provide a selected action time in the airflow to disinfect the air.

9. A disinfecting apparatus comprising:
    a first lamp and a second lamp each comprising:
        a coaxial tube defining an annulus there between;
        a first and second gas mixture selected to produce a first and second narrow wavelength photon emission different in each lamp, wherein the gas mixture and wavelength in the first lamp is different from the gas mixture and wavelength in the second lamp;
        a high voltage electrode located on a first tubular surface of the tube of each of the first lamp and the second lamp;
        a ground electrode located on a second tubular surface of the tube of each of the first lamp and the second lamp, the second tubular surface located opposite the annulus of the first lamp and the annulus of the second lamp from the first tubular surface; and
    a first photon reflector and second photon reflector secured in a spaced relationship to the first lamp and second lamp respectively and positioned to direct photons from both lamps to a zone or surface, whereby the disinfecting apparatus produces photons that are directed to a selected zone or surface and efficiently destroys or deactivates DNA organic bonds and proteins of microorganisms when the high voltage electrode is energized.

10. The disinfecting apparatus of claim 9, wherein the first and second narrow wavelength photon emissions are taken from the group consisting of 222 nm, 254 nm, and 282 nm.

11. The disinfecting apparatus of claim 9, wherein at least one lamp is an excimer lamp.

12. The disinfecting apparatus of claim 9, wherein the photon reflector is a gull wing-shaped director selected to direct at least 90% of emitted light to a planar surface.

13. The disinfecting apparatus of claim 9, the photon reflector comprising a barium sulfate composition for enhancing its reflective properties.

14. The disinfecting apparatus of claim 9 further comprising:
    an air duct surrounding the lamp mounted in a spaced relationship to the lamp to provide a selected action time in the airflow to disinfect the air.

* * * * *